(12) United States Patent
Stainsby et al.

(10) Patent No.: US 11,300,643 B2
(45) Date of Patent: Apr. 12, 2022

(54) ADAPTIVE SHIM COILS FOR MR IMAGING

(71) Applicant: SYNAPTIVE MEDICAL INC., Toronto (CA)

(72) Inventors: Jeff Alan Stainsby, Toronto (CA); Chad Tyler Harris, Toronto (CA)

(73) Assignee: SYNAPTIVE MEDICAL INC., Toronto (CA)

( * ) Notice: Subject to any disclaimer, the term of this patent is extended or adjusted under 35 U.S.C. 154(b) by 0 days.

(21) Appl. No.: 16/316,707

(22) PCT Filed: Jul. 11, 2016

(86) PCT No.: PCT/IB2016/054140
§ 371 (c)(1),
(2) Date: Jan. 10, 2019

(87) PCT Pub. No.: WO2018/011617
PCT Pub. Date: Jan. 18, 2018

(65) Prior Publication Data
US 2019/0302205 A1 Oct. 3, 2019

(51) Int. Cl.
*G01R 33/3875* (2006.01)
*A61B 5/055* (2006.01)
*G01R 33/38* (2006.01)
*G01R 33/381* (2006.01)

(52) U.S. Cl.
CPC ......... *G01R 33/3875* (2013.01); *A61B 5/055* (2013.01); *G01R 33/3806* (2013.01); *G01R 33/381* (2013.01)

(58) Field of Classification Search
CPC ............ G01R 33/3875; G01R 33/3806; G01R 33/381; A61B 5/055
See application file for complete search history.

(56) References Cited

U.S. PATENT DOCUMENTS

| 7,414,401 | B1 | 8/2008 | Lvovsky |
| 7,541,812 | B2 | 6/2009 | Nogami |
| 7,592,812 | B2 | 9/2009 | Ikedo |
| 8,536,870 | B2 | 9/2013 | Punchard |

(Continued)

OTHER PUBLICATIONS

Authorized Officer Blaine R. Copenheaver, International Search Report/Written Opinion for PCT/IB2016/054140, dated Oct. 26, 2016 (18 pages).

(Continued)

*Primary Examiner* — Rishi R Patel

(57) ABSTRACT

Some implementations provide a system that includes: a housing having a bore in which a subject to be image is placed; a main magnet configured to generate a volume of magnetic field within the bore, the volume of magnetic field having inhomogeneity below a defined threshold; one or more gradient coils configured to linearly vary the volume of magnetic field as a function of spatial location; one or more pulse generating coils configured to generate and apply radio frequency (RF) pulses to the volume of magnetic field in sequence to scan the portion of the subject; one or more shim gradient coils configured to perturb a spatial distribution of the linearly varying volume of magnetic field; and a control unit configured to operate the gradient coils, pulse generating coils, and shim gradient coils such that only the user-defined region within the volume of magnetic field is imaged.

12 Claims, 4 Drawing Sheets

(56) References Cited

U.S. PATENT DOCUMENTS

| | | | |
|---|---|---|---|
| 9,797,967 B2* | 10/2017 | Bindseil | G01R 33/381 |
| 10,078,121 B2* | 9/2018 | Bindseil | G01R 33/381 |
| 2007/0279060 A1* | 12/2007 | Dannels | G01R 33/56563 |
| | | | 324/320 |
| 2008/0164878 A1 | 7/2008 | Morich | |
| 2008/0253639 A1 | 10/2008 | Van Den Brink | |
| 2009/0027051 A1 | 1/2009 | Stuber | |
| 2011/0050229 A1 | 3/2011 | Chen et al. | |
| 2012/0249137 A1* | 10/2012 | Witschey | G01R 33/3875 |
| | | | 324/309 |
| 2014/0043028 A1* | 2/2014 | Blakes | G01R 33/3875 |
| | | | 324/320 |
| 2014/0327440 A1* | 11/2014 | Nakanishi | A61B 5/055 |
| | | | 324/309 |
| 2015/0054510 A1 | 2/2015 | Biber | |
| 2015/0200046 A1 | 7/2015 | Park et al. | |
| 2015/0260811 A1* | 9/2015 | Blumhagen | G01R 33/3875 |
| | | | 324/309 |
| 2015/0293194 A1* | 10/2015 | Kalechofsky | G01R 33/3621 |
| | | | 600/410 |
| 2016/0025830 A1* | 1/2016 | Roland | A61B 5/4312 |
| | | | 324/309 |
| 2017/0123027 A1* | 5/2017 | Zuehlsdorff | G01R 33/3875 |
| 2017/0261581 A1* | 9/2017 | Giri | A61B 5/055 |

OTHER PUBLICATIONS

PCT International Preliminary Report on Patentability Chapter II in International Appln. No. PCT/IB2016/054140, dated Jul. 11, 2018, 17 pages.

* cited by examiner

ADAPTIVE SHIM COILS FOR MR IMAGING

BACKGROUND

The present disclosure relates to magnetic resonance imaging and thermal dissipation.

SUMMARY

In general, one aspect of the subject matter described in this specification involves a magnetic resonance imaging (MRI) system including: a housing having a bore in which at least a portion of a subject to be image is placed; a main magnet accommodated by the housing and configured to generate a volume of magnetic field within the bore, the volume of magnetic field having inhomogeneity below a defined threshold; one or more gradient coils configured to linearly vary the volume of magnetic field as a function of spatial location in the volume of magnetic field; one or more pulse generating coils configured to generate and apply radio frequency (RF) pulses to the volume of magnetic field in sequence to scan the portion of the subject; one or more shim gradient coils configured to perturb a spatial distribution of the volume of magnetic field; and a control unit configured to: access an indication of at least one user-defined region to be imaged within the volume of magnetic field; and operate the gradient coils, pulse generating coils, and shim gradient coils such that only the user-defined region within the volume of magnetic field is imaged.

Implementations may include one or more of the following features. For example, the system may operate the gradient coils, pulse generating coils, and shim gradient coils such that only the user-defined region within the volume of magnetic field is imaged, the control unit is configured to operate the gradient coils, pulse generating coils, and shim gradient coils such that a frequency response of the RF pulses have a coherent effect only within the user-defined region.

In some implementations, the system may operate the gradient coils, pulse generating coils, and shim gradient coils such that a frequency response of the RF pulses have a coherent effect only within the user-defined region, the control unit is configured to operate the gradient coils, pulse generating coils, and shim gradient coils such that a resonant frequency of water falls outside of an RF bandwidth of the RF pulses in the regions of the volume of magnetic field outside of the user-defined region.

In some implementations, the user-defined region is not centered on an isocenter of the volume of magnetic field.

In some implementations, the user-defined region includes at least two regions that are unconnected regions within the volume of magnetic field.

In some implementations, the control unit is configured to access a second indication of a second user-defined region within the volume of magnetic field and operate the gradient coils, pulse generating coils, and shim gradient coils such that only the second user-defined region within the volume of magnetic field is imaged, the second user-defined region having a different shape than the at least one user-defined region.

In some implementations, the control unit is configured to access a second indication of a second user-defined region within the volume of magnetic field and operate the gradient coils, pulse generating coils, and shim gradient coils such that only the second user-defined region within the volume of magnetic field is imaged, the second user-defined region having a different size than the at least one user-defined region.

Another aspect of the subject matter described in this specification involves a method for operating a magnetic resonance imaging (MRI) system that includes a housing having a bore in which at least a portion of a subject to be image is placed, and a main magnet accommodated by the housing and configured to generate a volume of magnetic field within the bore having inhomogeneity below a defined threshold. The method may include: accessing an indication of at least one user-defined region to be imaged within the volume of magnetic field; operating one or more pulse generating coils to generate and apply radio frequency (RF) pulses to the at least one user-defined region in sequence to scan the portion of the subject; operating one or more gradient coils to linearly vary the volume of magnetic field as a function of spatial location in the volume of magnetic field; and operating one or more shim gradient coils to perturb a spatial distribution of the at least one user-defined region.

In some implementations, operating the one or more pulse generating coils to generate and apply radio frequency (RF) pulses includes operating the one or more pulse generating coils such that a frequency response of the RF pulses have a coherent effect only within the user-defined region.

In some implementations, operating one or more shim gradient coils to perturb a spatial distribution of the at least one user-defined region comprises operating the one or more shim gradient coils such that a resonant frequency of water falls outside of an RF bandwidth of the RF pulses in the regions of the volume of magnetic field outside of the user-defined region.

In some implementations, accessing an indication of at least one user-defined region to be imaged within the volume of magnetic field includes accessing an indication of at least one user-defined region that is not centered on an isocenter of the volume of magnetic field.

In some implementations, accessing an indication of at least one user-defined region to be imaged within the volume of magnetic field includes accessing an indication of at least one user-defined region that includes at least two regions that are unconnected regions within the volume of magnetic field.

In some implementations, the method further includes: accessing a second indication of a second user-defined region within the volume of magnetic field; and operating the gradient coils, pulse generating coils, and shim gradient coils such that only the second user-defined region within the volume of magnetic field is imaged, the second user-defined region having a different shape than the at least one user-defined region.

In some implementations, the method further includes: accessing a second indication of a second user-defined region within the volume of magnetic field; and operating the gradient coils, pulse generating coils, and shim gradient coils such that only the second user-defined region within the volume of magnetic field is imaged, the second user-defined region having a different size than the at least one user-defined region.

The details of one or more aspects of the subject matter described in this specification are set forth in the accompanying drawings and the description below. Other features, aspects, and advantages of the subject matter will become apparent from the description, the drawings, and the claims.

DETAILED DESCRIPTION

Figure 1A:
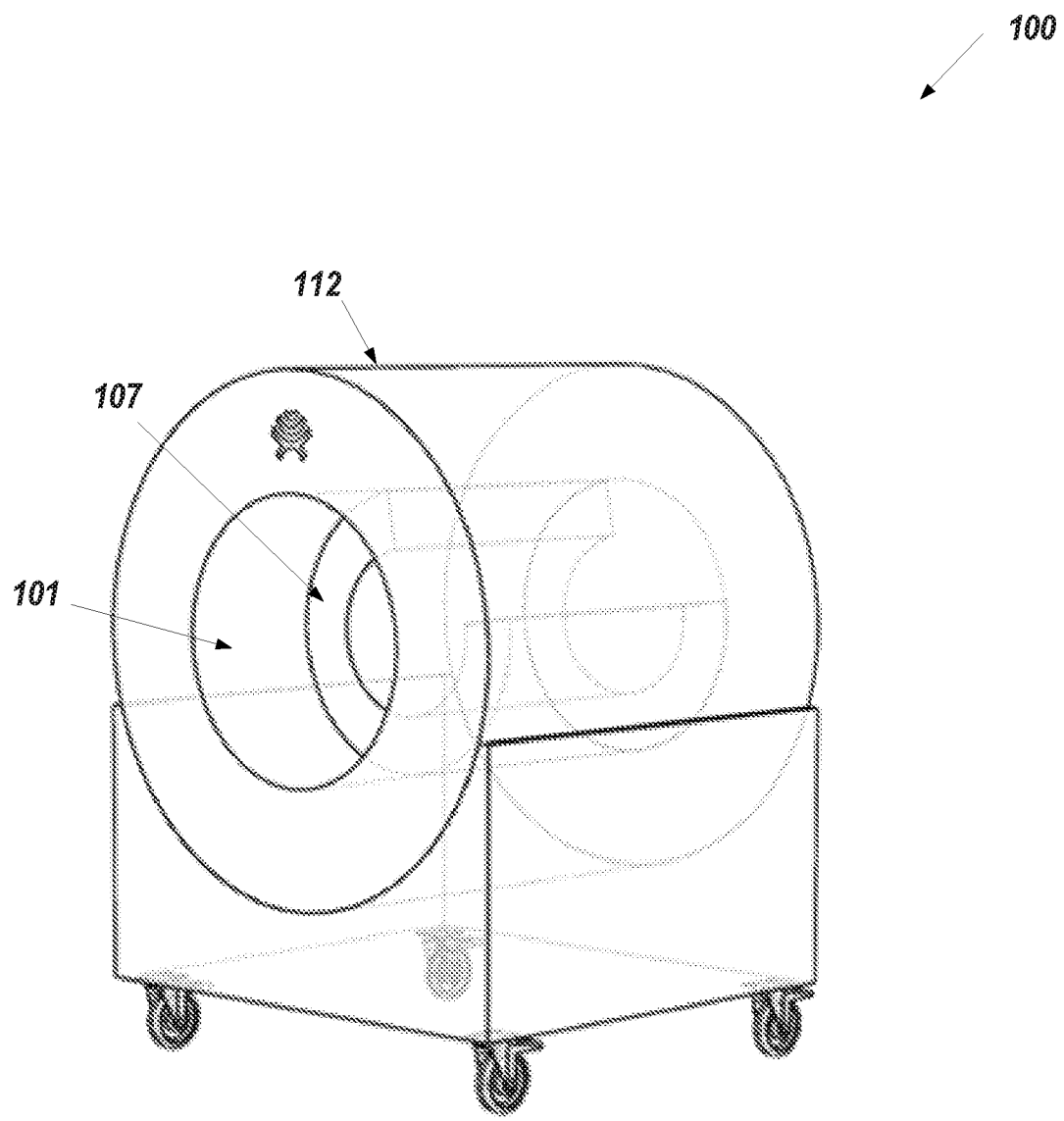
FIG. 1A shows a perspective view of an example of a magnetic resonance imaging (MRI) system with a solenoid magnet where a shimming coil is used to perturb a volume of uniform magnetic field inside the solenoid magnet.

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

In MRI systems, a main magnet generates a highly uniform static magnetic field over a certain volume for imaging purposes. The region of uniformity, also referred to as the uniform magnetic field or main field homogeneity, is typically characterized by the maximum static field deviation over a certain spherical volume. The main magnet is designed to achieve a specific homogeneity (e.g., an inhomogeneity below the threshold) in order to generate an MR image for the imaging volume. When a subject (e.g., a human head) is inserted into the MRI scanner, tissue and any implantable devices in the subject may also affect the homogeneity of the imaging. The homogeneity can typically be improved through fine adjustment of active shimming coils such that the specific homogeneity is met.

In some reduced field-of-view MR imaging techniques, a baseline volume of a highly uniform static magnetic field is reduced in order to collect an MR image for a smaller region within the baseline volume. In this context, the field-of-view of an imaged region refers to the volume of highly uniform static magnetic field with a specific homogeneity. Thus, in reduced field-of-view MR imaging, the field-of-view refers to the smaller region within the baseline volume.

The field-of-view used in magnetic resonance (MR) imaging often needs to be made large enough to avoid portions of an object of interest extending beyond the field-of-view to avoid signal wrap-around artifacts. However, this can also lead to significant amounts of time being used to encode spatial information across portions of anatomical objects that are not of interest. In addition, certain types of MR spatial encoding schemes can be sensitive to a variety of confounds such as field inhomogeneity, which can cause significant distortions and artifacts. In such instances, reduced field-of-view imaging can be used to restrict MR signals to smaller regions in order to generate spatial information from a reduced field to save time in encoding information specifically from a target region.

MR signals can be restricted using a shim gradient to perturb a volume of magnetic field that is used to generate an MR image such that the frequency response of the radiofrequency (RF) pulses used within an imaging sequence only have a coherent effect within the reduced field-of-view. As described more particularly below, the shim gradients can also be used to variably perturb the volume of magnetic field such that the reduced fields-of-view form different shapes and are positioned in different regions of the volume of magnetic field. According to selected embodiments, magnetic resonance imaging (MRI) systems can include an active coil, for example, integrated with gradient coils as one mechanical assembly to function as a location-specific static field shimming coil which, when activated, perturbs a spatial distribution of a volume of magnetic field over an MR imaging region such that the frequency response of radiofrequency (RF) pulses used in an imaging sequence have a coherent effect only within a user-defined region. Gradients applied to perturb the magnetic field using the shimming coils can be designed to create the user-defined regions of various shapes and sizes. As described in more detail below, some implementations may allow an operator, such as a clinician, to select a user-defined region to collect an image within an MR imaging region corresponding to a region of interest.

Figure 1B:
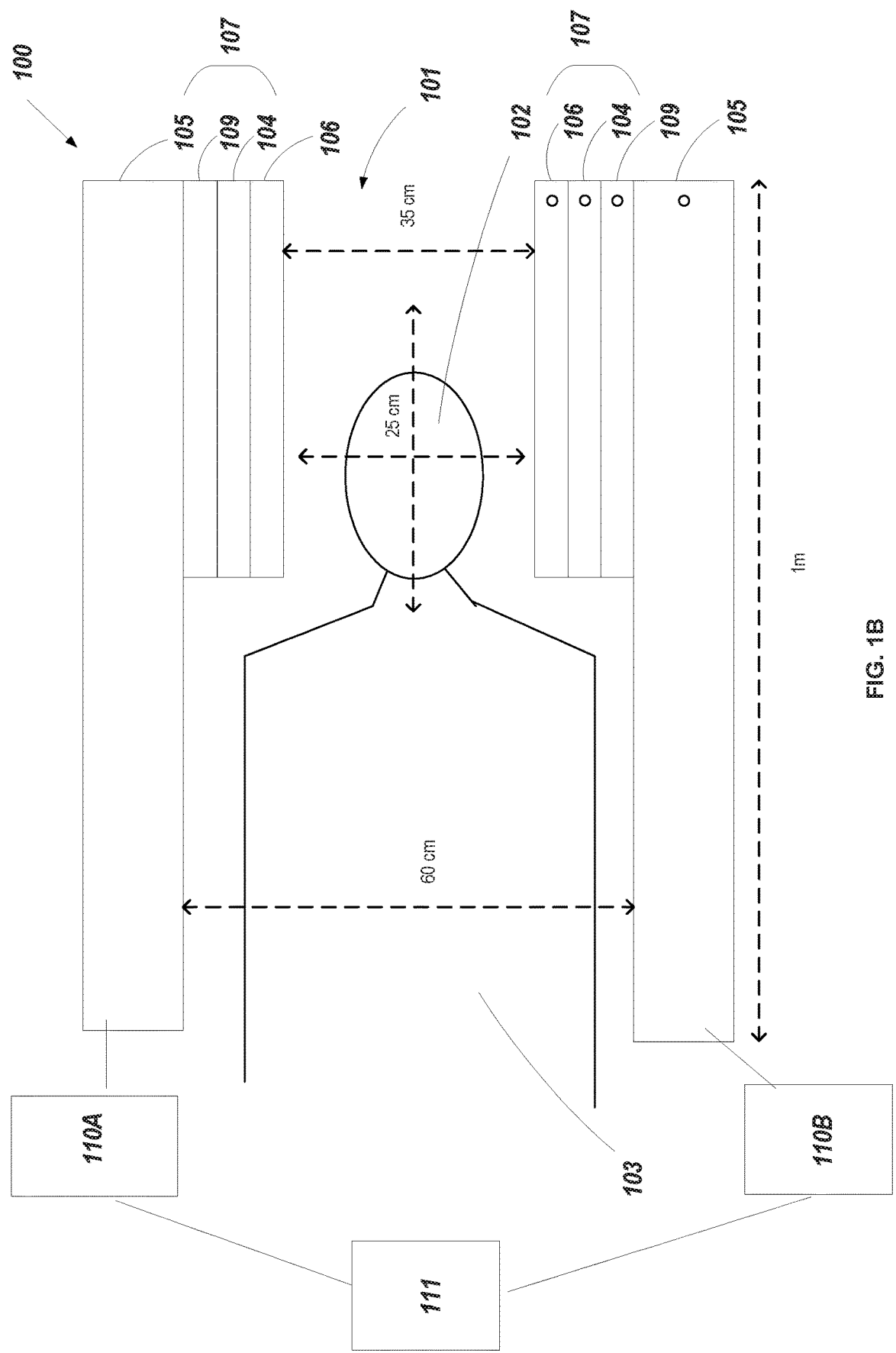
FIG. 1B shows a cross-sectional illustration of the example of a magnetic resonance imaging (MRI) system where the shimming coil is used to perturb the volume of uniform magnetic field.

FIGS. 1A-1B show a perspective view and a cross-sectional view of an example of a magnetic resonance imaging (MRI) system 100 in which a solenoid magnet 105 is provided in a cylindrical shape housing with an inner bore 101. Coil assembly 107, including a pulse generating coil 106 and a gradient coil 104, is provided within solenoid magnet 105.

Coil assembly 107 may generally be shaped as an annular structure and housed within the inner bore of solenoid magnet 105. In some implementations, annular coil assembly 107 only includes gradient coil 104. Gradient coil 104 generally provides field gradients in more than one directions, such as, for example, all three orthogonal spatial directions. Thus, gradient coil 104 may refer to three sets of coils, each configured to generate field fluctuations in a respective direction for the main field in the inner bore of the solenoid magnet 105. Such field fluctuations may cause magnetizations from various spatial locations to experience precessions at different frequencies, enabling encoding of spatial information of the magnetizations through RF excitation pulses. The pulse generating coil 106 can be configured to generate and apply RF pulses to the volume of magnetic field in sequence to scan a portion of patient 103 (e.g., the head region 102).

For context, the main magnet of the MRI system 100 generates a highly-uniform static magnetic field over a certain volume for imaging purposes. Although small static field variations on the order of parts per million (ppm) can be tolerated, it is not possible to generate MR data in locations where the main field deviates too greatly (e.g., over hundreds of parts per million (ppms) over a 20 centimeter diameter spherical volume). For example, 40 ppm over a 25-cm diameter spherical volume (DSV) can represent a maximum $\Delta B0=B0\ max-B0\ min=20\ \mu T$ field deviation at a static field of $B0=0.5$ T.

The main magnet is designed to achieve a specific homogeneity (that is, the main magnet is designed to have an inhomogeneity below the threshold). However, the actual homogeneity at the installation site may be affected by material in or around the MRI scanner. At the time of installation, passive and/or active shim coils (e.g., the shim gradient coils 109) may be applied to improve the homogeneity so that it meets the specific homogeneity the main magnet is designed to achieve before subjects are placed in the inner bore 101.

When a subject (i.e. a human head) is inserted into the MRI scanner, the tissue and any implantable devices in the subject may also affect the homogeneity of the imaging volume and the homogeneity is again typically improved through fine adjustment of active shim coils, such as for example, through shim gradient coils 109, so that the specific homogeneity is met.

To quantify main field homogeneity, some implementations may measure, for example, the spectral width of the free induction decay (FID) signal from the region of interest. In this measure, field homogeneity may hinge on the spectral width of the FID signal to be below a defined threshold. More specifically, if the spectral width of the FID signal is satisfactorily narrow for the desired imaging application, for example, below a defined spectral width value, shimming may be deemed satisfactory. Otherwise, additional shimming may be performed to further reduce the spectral width of the FID signal. In these implementations, annular coil assembly may not include pulse generating coil 106 or any receiver coil. For these implementations, radio-frequency (RF) excitation pulses are, for example, transmitted by local coils (e.g., pulse generating coils) for imaging the head region 102 of patient 103. In one instance, a head coil in a birdcage configuration is used for both transmitting RF excitation pulses and receiving MR signals for imaging the subject.

In another instance, the pulse generating coil 106 is a surface coil that is used for transmitting an RF excitation pulse into the subject and a phased array coil configuration is used for receiving MR signals in response.

Shim gradient coils 109 are housed within the cylindrical walls of solenoid magnet 105. Shim gradient coils 109 are powered by a group of power amplifiers 110A and 110B. In some cases, the power amplifiers 110A and 110B are housed in a control room and are connected to shim gradient coils 109 to provide shimming of the magnetic field within inner bore 101. In driving shim gradient coils 109, power amplifiers 110A and 110B are controlled by a control unit 111. The driving current for shim gradient coils 109 may be in the range of hundreds of miliamperes and generally may not exceed 1 ampere. Further, shim gradient coils 109 may not require active cooling using circulating coolant. In these implementations, an array of shimming coils can be used to provide adjustment to the field strength within the inner bore 101 such that the magnet field within the inner bore 101 becomes more homogenous. The shimming coils 109 produce spatial magnetic field perturbations which are in well-defined polynomial spatial patterns (e.g. $xy$, $x^2$, $y^2$). In some implementations, the shimming coils 109 can by dynamically configured to produce arbitrary spatially varying patterns in the magnetic field.

The control unit 111 generally includes one or more processors as well as programming logic to configure the power amplifiers 110A and 110B to adjust the operation of the shim gradient coils 109. As described more specifically below, the control unit 111 can be configured to access an indication of a user-defined region to be imaged within the volume of magnetic field, and operate the gradient coil 104, the pulse generating coil 106, and the shim gradient coil 109 such that only the user-defined region within the volume of magnetic field is imaged. In some implementations, the control unit 111 is configured to operate the gradient coil 104, the pulse generating coil 106, and the shim gradient coil 109 such that a frequency response of the RF pulses have a coherent effect only within the user-defined region.

Figure 2A:
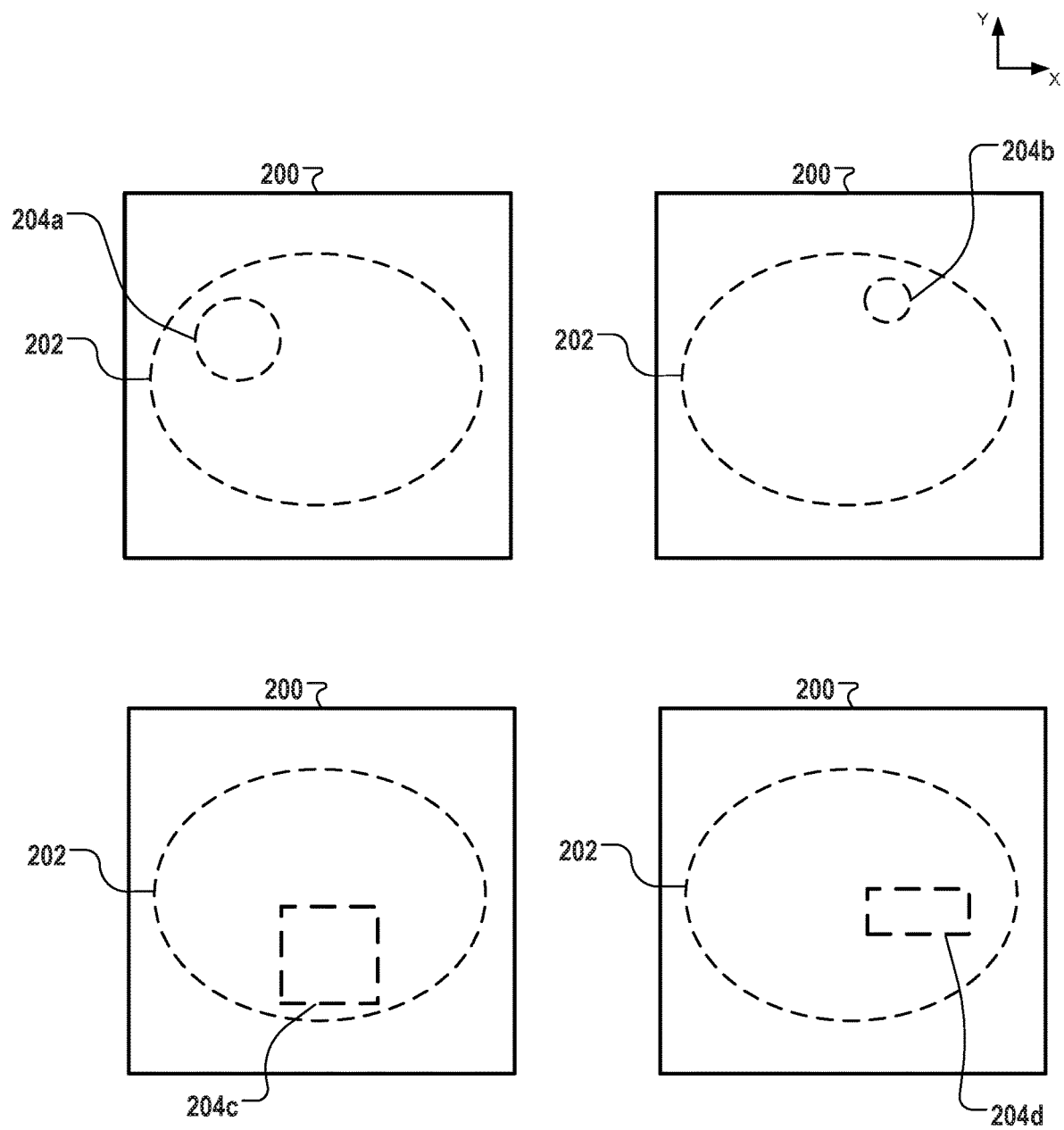
FIG. 2A illustrates examples of adjustable imaging regions within a magnetic resonance (MR) image.
Figure 2B:
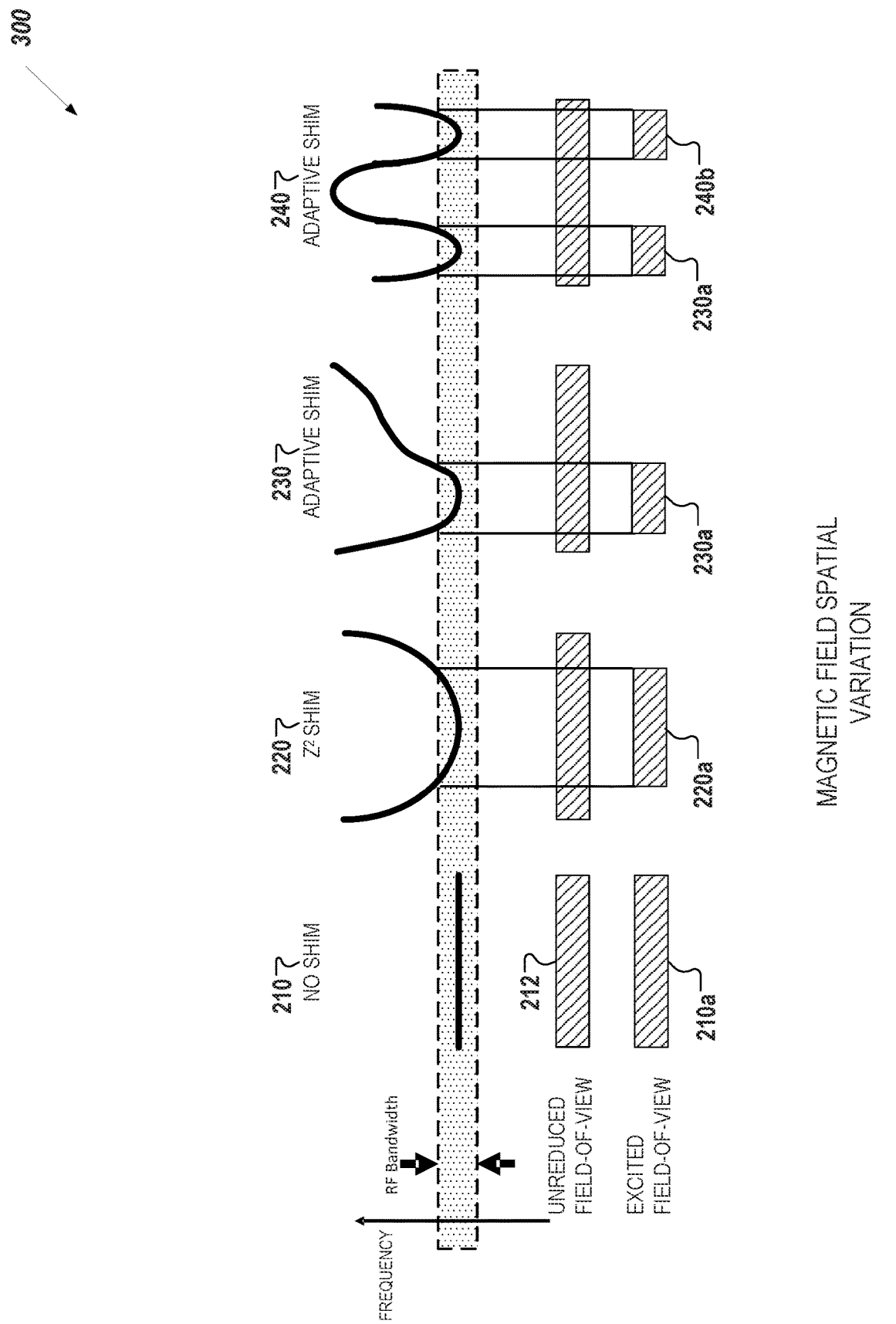
FIG. 2B illustrates examples of shimming coil gradients used to perturb a spatial distribution of a volume of magnetic field over an MR imaging region.

As depicted in FIGS. 2A and 2B, the user-defined region within the within the volume of magnetic field that is imaged can be variably configured based on the shim gradient patterns. For example, in some instances, the user-defined region includes at least two regions that are unconnected regions within the volume of magnetic field. In other instances, the user-defined region can be configured to have different shapes and different sizes.

In more detail, the control unit 111 can be used to configure the shim gradient coils 109 to generate different shimming gradients that variably perturb a spatial distribution of the volume of magnetic field applied over the inner bore 101. In some instances, the control unit 111 is housed in a control room separate from the solenoid magnet 105 of the MRI system 100.

In some implementations, the control unit 111 includes a user interface that allows an operator such as a clinician or technician to adjust the shimming gradient applied by the shim gradient coils 109 to the inner bore 101. For example, in such implementations, the control unit 111 presents the operator with a set of different gradient patterns that are selectable by the operator. In response to receiving user selection of a gradient pattern on the user interface, the control unit 111 then transmits control signals to the power amplifiers 110A to 110B to adjust the operation of the shim gradient coils 109 to generate the selected gradient pattern.

The user interface on the control unit 111 can be additionally be used to specify adaptive gradient patterns that are customized for a particular region within the volume of static magnetic field used to generate an MR image. For example, as depicted in FIG. 2A, the custom gradient patterns can be used to adjust the field of view of the MRI image captured of the patient 103. In these examples, the user interface of the control unit 111 displays a custom gradient pattern generator that allows the operator to adjust the shape, magnitude, and other features of the gradient pattern. The user interface also displays a predicted field of view of the MRI image resulting from the custom gradient pattern. The predicted field of view of the MRI can be adjusted in real-time with changes made by the operator on the custom gradient pattern generator such that the user interface allows the operator to configure the field of view to specific regions of interest. For instance, the predicted field of view may be superimposed over a baseline MR image to spatially coordinate the predicted field of view to anatomical features of interest.

The embodiments provided herein may be adapted for intraoperative MRI, and MRI systems for use in an emergency room setting. Such MRI systems may include a smaller and more compact bore size magnet compared to the magnets from conventional whole body scanners.

FIG. 2A illustrates examples of adjustable imaging regions 204a-d of a region 202 within an MRI field-of-view 200. The MRI system 100 initially generates a highly uniform static magnetic field over the region 202 for imaging purposes within the field-of-view 200 of the MRI system 100. The generated magnetic field can then be perturbed using the shim gradient coils 109 in order to adjust the spatial distribution of the magnetic field over the region 202. In this regard, different shimming coil patterns may be used to generate various user-defined imaging regions such as the adjustable imaging regions 204a-204d.

Referring now to FIG. 2A, adjustable imaging regions 204a-204d represent examples of customizable regions that are imaged within a region 202. As depicted, the adjustable imaging regions 204a-d may vary in size and shape based on the specific perturbation of the spatial distribution of magnetic field over the region 202 along the respective horizontal and vertical axis of the field-of-view 200 (e.g., x-axis and y-axis).

Although the adjustable imaging regions 204a-204d are depicted as symmetrical shapes (e.g., circles, rectangles, squares, etc.), in FIG. 2A, in some instances, perturbation of the spatial distribution of magnetic field over the region 202 can also be used to generate arbitrary shapes and sizes. In addition, the perturbation can also be applied such that multiple imaging regions within the region 202 can be used for localized imaging of specific structures within the MRI field-of-view 200.

In changing the spatial distribution of the magnetic field, the applied shim gradient also changes the spatial distribution of the resonant frequency of water. Thus, the shim gradient can be applied to shift the resonant frequency of water outside the bandwidth of the RF pulse in certain regions over the region 202 such that water in these regions are unaffected by the RF pulse and do not contribute to the resultant MR image. In contrast, the resonant frequency of water included within the adjustable imaging regions 204a-d are within the bandwidth of the RF pulse such that the resultant MR image only includes spatial information from the water included within the adjustable imaging f20 regions 204a-204d.

The perturbation of the spatial distribution of the static magnetic field over the region 202 causes the frequency response of the RF pulses used in an imaging sequence to have a coherent effect only within the adjustable imaging regions 204a-204d. For example, during an imaging sequence over the region 202, a shim gradient may also be applied over the region 202 using the shim gradient coils 109 to create a spatially varying effect to the distribution of magnetic field over the volume of magnetic field. In some implementations, the shim gradient may be applied at the same time as a standard slice-selective excitation during an MR imaging sequence. In other implementations, the shim gradient may be applied during an MR imaging refocusing pulse.

Referring now to FIG. 2B, different shim gradient patterns can be used to excite specific regions of an unreduced field-of-view 212 during an MR image sequence. For instance, in 210, because there is no shim gradient applied to the region 202, the resonant frequency of all of the water within the unreduced field-of-view 212 falls within the bandwidth of the RF pulse, resulting in an excited field-of-view 210a that is includes the entire unreduced field-of-view 212. In contrast, when using a shim gradient 220, the resonant frequency of water falls outside the bandwidth near the edges of the unreduced field-of-view 212, which results in an excited field-of-view 220a that only includes the center portion of the unreduced field-of-view 212.

As discussed previously, the shimming coils 109 produce spatial magnetic field perturbations which are in well-defined polynomial spatial patterns (e.g. xy, $x^2$, $y^2$). In some implementations, the shimming coils 109 can by dynamically configured to produce arbitrary spatially varying patterns in the magnetic field using adaptive gradients 230 and 240. Adaptive gradients 230 and 240 can be used to apply specific changes to the spatial distribution of the resonant frequency of water such that the excited regions 230a and 240b are not centered on the isocenter of the magnetic field over the field-of-view 212. For example, the adaptive gradient 230 causes only a decrease in resonant frequency near the left portion of the field-of-view 212 such an excited field-of-view 230a only includes a left portion of the field-of-view 212 but not the right portion of the field-of-view 212 that includes water with a resonant frequency above the RF bandwidth. In another example, the adaptive gradient 240 causes decreases in resonant frequency in multiple regions of the field-of-view 212 such that multiple excited field-of-views 240a and 240b are created within the field-of-view 212. In this example, the adaptive gradient 240 causes a sinusoidal change in resonant frequency along the horizontal axis of the field-of-view 212.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

What is claimed is:

1. A magnetic resonance imaging (MRI) system, comprising:
    a housing having a bore in which at least a portion of a subject to be image is placed;
    a main magnet accommodated by the housing and configured to generate a magnetic field within the bore;
    one or more gradient coils configured to linearly vary the magnetic field as a function of spatial location therein;
    one or more pulse generating coils configured to generate and apply radio frequency (RF) pulses to the magnetic field in sequence to scan the portion of the subject;
    one or more shim gradient coils configured to perturb the magnetic field; and
    a control unit configured to:
        access an indication of at least one user-defined region that is adjustable both axially and laterally within a field of view of the MRI system, the field of view corresponding to a 2D image slice encompassing the at least one user-defined region, and
        operate the gradient coils, pulse generating coils, and shim gradient coils such that (i) a field inhomogeneity of the at least one user-defined region within the 2D image slice is reduced to become suitable for magnetic resonance imaging while a field inhomogeneity of the magnetic field outside the at least one user-defined region within the 2D image slice is simultaneously increased to become unsuitable for magnetic resonance imaging, and (ii) a frequency response of the RF pulses have a coherent effect only within the at least one user-defined region, wherein RF emissions are acquired, in response to the RF pulses and when the magnetic field is perturbed by the shim gradient coils, from the at least one user-defined region within the 2D image slice that corresponds to the field of view of the MRI system, the RF emissions encoding one or more magnetic resonance images solely of the at least one user-defined region within the 2D image slice that corresponds to the field of view of the MRI system based on, at least in part, the function of spatial location according to which the magnetic field is varied by the one or more gradient coils.

2. The magnetic resonance imaging (MRI) system of claim 1, wherein the control unit is configured to operate the gradient coils, pulse generating coils, and shim gradient coils such that a resonant frequency of water falls outside of an RF bandwidth of the RF pulses in the magnetic field outside of the at least one user-defined region.

3. The magnetic resonance imaging (MRI) system of claim 1, wherein the user-defined region is not centered on an isocenter of the magnetic field.

4. The magnetic resonance imaging (MRI) system of claim 1, wherein the at least one user-defined region includes at least two regions that are unconnected regions within the magnetic field.

5. The magnetic resonance (MRI) system of claim 1, wherein the control unit is configured to access a new indication of a new user-defined region within the magnetic field and operate the gradient coils, pulse generating coils, and shim gradient coils to obtain one or more magnetic resonance images of the new user-defined region within the magnetic field, the new user-defined region having a different shape than the at least one user-defined region.

6. The magnetic resonance (MRI) system of claim 1, wherein the control unit is configured to access a new indication of a new user-defined region within the magnetic field and operate the gradient coils, pulse generating coils, and shim gradient coils to obtain one or more magnetic resonance images of the new user-defined region within the magnetic field, the new user-defined region having a different size than the at least one user-defined region.

7. A method for operating a magnetic resonance imaging (MRI) system comprising a housing having a bore in which at least a portion of a subject to be image is placed, and a main magnet accommodated by the housing and configured to generate a magnetic field within the bore, the method comprising:
  accessing an indication of at least one user-defined region that is adjustable both axially and laterally within a field of view of the MRI system, the field of view corresponding to a 2D image slice encompassing the at least one user-defined region;
  operating one or more pulse generating coils to generate and apply radio frequency (RF) pulses to the magnetic field to scan the portion of the subject;
  operating one or more gradient coils to linearly vary the magnetic field as a function of spatial location therein;
  operating one or more shim gradient coils to perturb the at least one user-defined region such that a field inhomogeneity of the at least one user-defined region within the 2D image slice is reduced to become suitable for magnetic resonance imaging while a field inhomogeneity of the magnetic field outside the at least one user-defined region within the 2D image slice is increased to become unsuitable for magnetic resonance imaging; and
  in response to the RF pulses and when the magnetic field is perturbed by the shim gradient coils, acquiring RF emissions from the at least one user-defined region within the 2D image slice that corresponds to the field of view of the MRI system, wherein the RF pulses have a coherent effect only within the at least one user-defined region, and wherein the RF emissions encode one or more magnetic resonance images solely of the at least one user-defined region within the 2D image slice that corresponds to the field of view of the Mill system based on, at least in part, the function of spatial location according to which the magnetic field is varied by the one or more gradient coils.

8. The method of claim 7, wherein operating one or more shim gradient coils to perturb the at least one user-defined region comprises operating the one or more shim gradient coils such that a resonant frequency of water falls outside of an RF bandwidth of the RF pulses in the magnetic field outside of the user-defined region.

9. The method of claim 7, wherein accessing an indication of at least one user-defined region to be imaged within the magnetic field comprises accessing an indication of at least one user-defined region that is not centered on an isocenter of the magnetic field.

10. The method of claim 7, wherein accessing an indication of at least one user-defined region to be imaged within the magnetic field comprises accessing an indication of at least one user-defined region that includes at least two regions that are unconnected regions within the magnetic field.

11. The method of claim 7, further comprising:
  accessing a new indication of a new user-defined region within the magnetic field; and
  operating the gradient coils, pulse generating coils, and shim gradient coils to obtain one or more magnetic resonance images of the new user-defined region within the magnetic field, the new user-defined region having a different shape than the at least one user-defined region.

12. The method of claim 7, further comprising:
  accessing a new indication of a new user-defined region within the magnetic field; and
  operating the gradient coils, pulse generating coils, and shim gradient coils to obtain one or more magnetic resonance images of the new user-defined region within the magnetic field, the new user-defined region having a different size than the at least one user-defined region.

* * * * *